(12) United States Patent
Bruce et al.

(10) Patent No.: US 11,786,219 B2
(45) Date of Patent: *Oct. 17, 2023

(54) METHOD FOR DETERMINING A PHYSICAL CHARACTERISTIC ON A PUNCTUAL LOCATION INSIDE A MEDIUM, A METHOD FOR DETERMINING AN IMAGE OF A MEDIUM, AND AN APPARATUS IMPLEMENTING SAID METHODS

(71) Applicant: SUPERSONIC IMAGINE, Aix-en-Provence (FR)

(72) Inventors: Matthew Bruce, Les Milles (FR); Charles Tremblay-Darveau, Toronto (CA)

(73) Assignee: SUPERSONIC IMAGINE, Aix-en-Provence (FR)

( * ) Notice: Subject to any disclaimer, the term of this patent is extended or adjusted under 35 U.S.C. 154(b) by 96 days.

This patent is subject to a terminal disclaimer.

(21) Appl. No.: 17/326,000

(22) Filed: May 20, 2021

(65) Prior Publication Data

US 2021/0267576 A1    Sep. 2, 2021

Related U.S. Application Data

(63) Continuation of application No. 15/111,214, filed as application No. PCT/EP2015/051369 on Jan. 23, 2015, now Pat. No. 11,058,401.

(Continued)

(51) Int. Cl.
*A61B 8/08*    (2006.01)
*G01S 7/52*    (2006.01)
(Continued)

(52) U.S. Cl.
CPC .......... *A61B 8/5207* (2013.01); *A61B 8/0891* (2013.01); *A61B 8/14* (2013.01);
(Continued)

(58) Field of Classification Search
CPC ............. G01S 15/8963; G01S 7/52039; G01S 7/52071; A61B 8/00; A61B 8/08;
(Continued)

(56) References Cited

U.S. PATENT DOCUMENTS 5,577,505 A    11/1996   Brock-Fisher et al.
5,706,819 A    1/1998    Hwang et al.
(Continued)

FOREIGN PATENT DOCUMENTS

JP    2001286472 A    10/2001
JP    5041258 A       10/2012
(Continued)

OTHER PUBLICATIONS

International Search Report related to Application No. PCT/EP2015/051369; reported dated May 11, 2015.

*Primary Examiner* — Carolyn A Pehlke
(74) *Attorney, Agent, or Firm* — von Briesen & Roper, s.c.

(57) ABSTRACT

A method for determining a physical characteristic on a punctual location inside a medium, comprising the steps of: sending an emitted sequence comprising emitted pulses having different amplitudes, receiving a received sequence comprising received pulses corresponding to echoes of emitted pulses, calculating a phase difference between the received pulses relative to the emitted pulses, and determining the physical characteristic on the bases of a phase difference.

15 Claims, 3 Drawing Sheets

Related U.S. Application Data

(60) Provisional application No. 61/930,805, filed on Jan. 23, 2014.

(51) Int. Cl.
  *G01S 15/89* (2006.01)
  *A61B 8/14* (2006.01)
  *A61B 8/00* (2006.01)

(52) U.S. Cl.
  CPC ............ *A61B 8/4444* (2013.01); *A61B 8/481* (2013.01); *G01S 7/52039* (2013.01); *G01S 7/52071* (2013.01); *G01S 15/8963* (2013.01)

(58) Field of Classification Search
  CPC ....... A61B 8/5207; A61B 8/0891; A61B 8/14; A61B 8/4444; A61B 8/481
  See application file for complete search history.

(56) References Cited

U.S. PATENT DOCUMENTS

| | | |
|---|---|---|
| 6,095,980 A | 8/2000 | Burns et al. |
| 6,398,732 B1 | 6/2002 | Brock-Fisher et al. |
| 6,497,665 B1 | 12/2002 | Hunt et al. |
| 6,506,158 B2 | 1/2003 | Kawagishi et al. |
| 6,638,228 B1 | 10/2003 | Brock-Fisher et al. |
| 11,058,401 B2 * | 7/2021 | Bruce .................... A61B 8/481 |

FOREIGN PATENT DOCUMENTS

| | | |
|---|---|---|
| WO | 2008016992 A1 | 2/2008 |
| WO | 2010121265 A1 | 10/2010 |

* cited by examiner

METHOD FOR DETERMINING A PHYSICAL CHARACTERISTIC ON A PUNCTUAL LOCATION INSIDE A MEDIUM, A METHOD FOR DETERMINING AN IMAGE OF A MEDIUM, AND AN APPARATUS IMPLEMENTING SAID METHODS

CROSS-REFERENCE TO RELATED APPLICATION

This is a Continuation application under 35 U.S.C. § 120 claiming priority to U.S. patent application Ser. No. 15/111,214 filed on Jul. 13, 2016; which is a 35 U.S.C. § 371 National Phase filing of PCT/EP2015/051369 filed on Jan. 23, 2015; which claims priority under 35 U.S.C. § 119 to U.S. Provisional Application No. 61/930,805 filed on Jan. 23, 2014.

FIELD OF THE INVENTION

The present invention concerns a method for characterizing a punctual location inside a medium with ultrasound, and for determining an image of a region inside said medium, in using ultrasound waves propagation inside said medium. The present invention also concerns the apparatus implementing said methods.

BACKGROUND OF THE INVENTION

Ultrasound imaging of a medium is a very common technique for imaging a medium, and in particular for imaging a human body. Lots of ultrasound imaging techniques are known.

For example, the U.S. Pat. No. 6,095,980 discloses an imaging system and method for detecting linear and non-linear scatterers inside the medium, called "pulse inversion Doppler". This system measures the ultrasound response under multiple excitation levels, so as to improve sensitivity in the detection of non-linear responses. Additionally, this method often uses the injection of contrast agents inside the medium for again improving the sensitivity of ultrasound imaging.

Unfortunately, with such an imaging system, the user still gets a weak contrast and in spite of the use of contrast agents, some tissue signals (i.e. without contrast agents) remain in the image and then the bloods vessels contours are insufficiently defined in the image.

OBJECTS AND SUMMARY OF THE INVENTION

One object of the present invention is firstly to provide a method for determining a physical characteristic on a punctual location inside the medium.

To this effect, the method comprises the following steps:
a) sending an emitted sequence of ultrasound waves into the medium towards the location, the emitted sequence comprising at least two emitted pulses having different amplitudes,
b) receiving a received sequence of ultrasound waves from the location, the received sequence comprising two received pulses corresponding to echoes of said emitted pulses,
c) calculating a phase difference between the received pulses relative to the two emitted pulses, and
d) determining the physical characteristic on the bases of said phase difference.

Thanks to these features, the physical characteristic on the punctual location of the medium is determined with an improved accuracy.

In various embodiments of the method, one and/or other of the following features may optionally be incorporated.

In an aspect of the method, the step c) of calculating a phase difference comprises the following sub-steps:
c1) determining a phase for each one of the received pulses in the received sequence, and
c2) calculating the phase difference by combining said phases.

In an aspect of the method, the step c) of calculating a phase difference comprises the following sub-steps:
c3) received signals corresponding to said received pulses are weighted by weighting factors and summed for producing a combined signal, said weighting factors being determined so that to compensate the different amplitudes of the emit pulses, and
c4) the phase difference is a phase of said combined signal.

In an aspect of the method, the physical characteristic is proportional to the phase difference.

In an aspect of the method, the succession of steps a) to c) are repeated several times for providing a plurality of phase differences, and wherein:
during step d), the physical characteristic is determined by a mean or a standard deviation or a variance of said plurality of phase differences.

In an aspect of the method, the emitted sequence comprises a number greater than two emitted pulses, the received sequence comprises at least the same number of received pulses than the number of emitted pulses, and wherein:
during step c), a plurality of phase differences between couples corresponding to two received and emitted pulses is calculated, each couple of emitted pulses having a different amplitude, and
during step d), the physical characteristic is determined by a mean or a standard deviation or a variance of said plurality of phase differences.

In an aspect of the method:
the physical characteristic is of a first type if it is lower than or equal to a first limit, and
the physical characteristic is of a second type if it is higher than a second limit.

In an aspect of the method, the second limit is higher than the first limit.

In an aspect of the method, the first limit is 0.3 radian, and preferably 0.1 radian.

In an aspect of the method, the second limit is 0.3 radian, and preferably 0.5 radian.

Another object of the invention is secondly to provide an apparatus for determining physical characteristic on a punctual location inside a medium. The apparatus comprises:
a probe comprising an ultrasound transducer,
an electronic unit controlling the transducer, and
a processing unit for controlling the electronic unit and for processing signals from said electronic unit.

The processing unit implements the method for determining a physical characteristic on a punctual location above specified.

Another object of the invention is thirdly to provide a method for determining an image of a region inside a medium, the image being composed of a plurality of pixels, and wherein the method comprises for a plurality of locations inside the region.

The method comprises the following steps:
a) sending an emitted sequence of ultrasound waves towards the location into the region, the emitted sequence comprising at least two emitted pulses of different amplitudes,
b) receiving a received sequence of ultrasound waves from the location, the received sequence comprising at least two received pulses corresponding to said emitted pulses,
c) calculating a phase difference between the received pulses relative to the emitted pulses, and
d) determining the pixel of the image on the bases of said phase difference.

Thanks to these features, the image of the medium is determined with an improved sensitivity and accuracy. The image contrast of the image is improved compared to known ultrasound techniques.

In various embodiments of the method, one and/or other of the following features may optionally be incorporated.

In an aspect of the method, the step c) of calculating a phase difference comprises the following sub-steps:
c1) determining a phase for each one of the received pulses in the received sequence, and
c2) calculating the phase difference by combining said phases.

In an aspect of the method, the step c) of calculating a phase difference comprises the following sub-steps:
c3) received signals corresponding to said received pulses are weighted by weighting factors and summed for producing a combined signal, said weighting factors being determined so that to compensate the different amplitudes of the emit pulses, and
c4) the phase difference is a phase of said combined signal.

In an aspect of the method: during step d), the pixel is proportional to the phase difference.

In an aspect of the method, the succession of steps a) to c) are repeated several times for providing a plurality of phase differences for each location inside the region, and:
during step d), the pixel is determined by calculating a mean or a standard deviation or a variance of said plurality of phase differences.

In an aspect of the method, the emitted sequence comprises a number greater than two emitted pulses, the received sequence comprises at least the same number of received pulses, and:
during step c), a plurality of phase differences between couples of corresponding to two received and emitted pulses is calculated, each couple of emitted pulses having a different amplitudes, and
during step d), the pixel is determined by calculating a mean or a standard deviation or a variance of said plurality of phase differences.

In an aspect of the method, each pixel in the image corresponds to a location inside the region.

In an aspect of the method:
the region is subdivided in a plurality of sub-regions,
between step c) and step d), a sub-region phase difference is calculated, said sub-region phase difference being a mean value of the plurality of phase differences of the locations belonging to said sub-region, and
each pixel in the image corresponds to a sub-region.

In an aspect of the method:
each pixel is of a first type if it is lower than or equal to a first limit, and
each pixel is of a second type if it is higher than a second limit.

In an aspect of the method, the second limit is higher than the first limit.

In an aspect of the method, the first limit is 0.3 radian, and preferably 0.1 radian.

In an aspect of the method, the second limit is 0.3 radian, and preferably 0.5 radian.

In an aspect of the method, two emitted pulses of the emitted sequence have an amplitude ratio of greater or equal to two.

In an aspect of the method, before step a), a contrast agent is introduced into the medium.

In an aspect of the method, the contrast agents comprises microbubbles.

Another object of the invention is fourthly to provide an apparatus for determining an image of a region inside a medium, said apparatus comprising
a probe comprising an ultrasound transducer,
an electronic unit controlling the transducer, and
a processing unit for controlling the electronic unit 13 and for processing signals from said electronic unit.

The processing unit implements the method for determining an image of a region inside a medium above specified.

BRIEF DESCRIPTION OF THE DRAWINGS

Other features and advantages of the invention will be apparent from the following detailed description of its embodiments given by way of non-limiting example, with reference to the accompanying drawings.

In the drawings.

In the figures, the same references denote identical or similar elements.

MORE DETAILED DESCRIPTION

Figure 1:
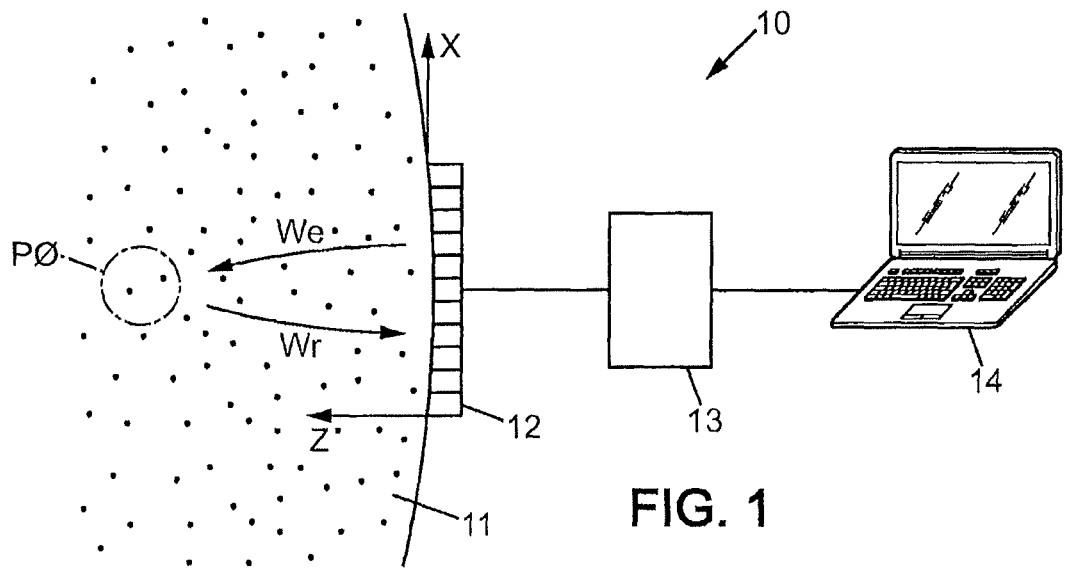
FIG. 1 is schematic drawing of an apparatus for implementing a first configuration of the method according to the invention (method for punctual measurement)

FIG. 1 shows an apparatus 10 for implementing the method of the invention, for instance for the purpose of determining a characteristic of a location inside a medium 11, or for instance for the purpose of imaging an area in a medium 11.

The medium 11 is for instance a living body and in particular human or animal bodies, or can be any other biological or physic-chemical medium (e.g. in vitro medium). The volume of medium comprises variations in its physical properties. For example, the medium may comprise tissues and blood vessels, each one having various physical properties. For example, the tissue may comprise an area suffering from an illness (e.g. cancerous cells), or any other singular area, having various physical properties in comparison to other area of the medium. Some portions of the medium 11 may include some added contrast agent (e.g. micro bubbles) for improving the contrast of physical properties of these portions. When insonified by ultrasound waves, such contrast agents generate non-linear echoes. Therefore, a well-known use of such contrast agents is the injection of a fluid containing a predetermined quantity of contrast agents inside blood vessels. Then, the physical characteristic of such blood vessels can be more easily detected in comparison to a physical characteristic of a tissue that does not comprise the contrast agent, said contrast agent only flowing in the vessels.

The physical characteristics, that can be detected by the method that senses the medium via ultrasound waves, are mechanical properties of the medium, like stiffness, or else. The method distinguishes values and/or variations of said physical properties. For example, the method may detect mechanical interface between two materials in the medium: e.g. it can detect bubbles shell.

The apparatus 10 may include:
- a probe 12 comprising one ultrasound transducer or a plurality of ultrasound transducers (a transducer array), each transducer being adapted to transform a signal into an ultrasound wave (emit) and/or to transform an ultrasound wave into a signal (receive),
- an electronic unit 13 controlling the transducers in the probe in both mode (receive and/or emit), and
- a processing unit 14 for controlling the electronic unit 13, processing signals, and determining characteristics of the medium and/or images of said characteristics.

In a variant, a single electronic device could fulfil all the functionalities of the electronic unit 13 and of the processing unit 14. The processing unit 14 may be a computer.

The probe 12 can comprise a curved transducer so as to perform an ultrasound focusing to a predetermined position in front of the probe. The probe 12 can comprise a linear array of transducers, few tens of transducers (for instance 100 to 300) juxtaposed along an axis X so as to perform ultrasound focusing into a bi-dimensional (2D) plane. The probe 12 can comprise a bi-dimensional array so as to perform ultrasound focusing into a tri-dimensional (3D) volume.

A first configuration of the method represented on FIG. 1 is for determining a physical characteristic of a location P0 inside the medium 11, said location P0 being substantially a punctual location or a small region inside the medium around said location P0 (near location P0).

The above processing unit 14 controls the electronic unit 13 and the probe 12 for:
a) sending an emitted sequence ES of ultrasound waves We into the medium 11 towards the location P0, the emitted sequence ES comprising at least two emitted pulses Se1, Se2 having different amplitudes,
b) receiving a received sequence RS of ultrasound waves 4 from the location P0, the received sequence RS comprising at least two received pulses Sr1, Sr2, each one corresponding to said emitted pulses Se1, Se2.

The ultrasound waves We, Wr toward and from the location can be a focused wave (beam) or a non focused beam.

A well-known beamforming method can be used:
- the emitted ultrasound wave We is generated by a plurality of transducers signals that are delayed and transmitted to each transducer of a transducer array, and
- the received ultrasound wave Wr is composed of a plurality of transducers signals that are combined by delay and summation to produce a received sequence RS.

The at least two different amplitudes of emitted pulses can be produced by varying the transmit voltage or preferably by varying the aperture size (i.e. by varying the number of transducers elements contributing to emit the emitted ultrasound wave). The aperture may also be divided into two or more groups of elements.

Figure 2A:
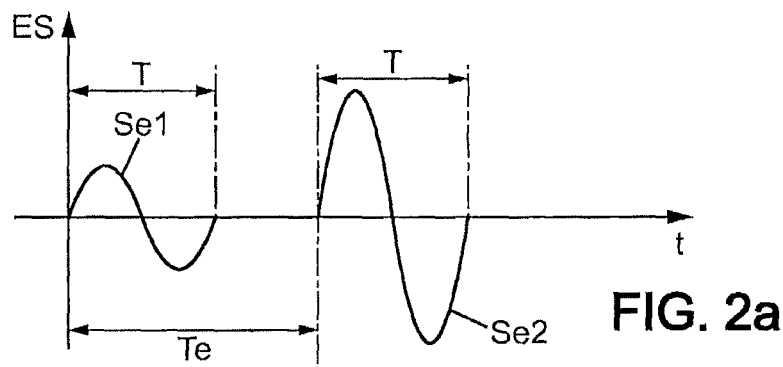
FIG. 2*a* is a time domain curve showing an emitted sequence of signals used by the method implemented by the apparatus of FIG. 1.

FIG. 2a shows an example of an emitted sequence ES comprising two signals Se1 and Se2, each one being an ultrasound pulse. For simplicity, these pulses (signals) are a portion of a sine signal (comprising only a single frequency component), but such pulses may be more complex signals comprising a plurality of frequency components.

Figure 2B:
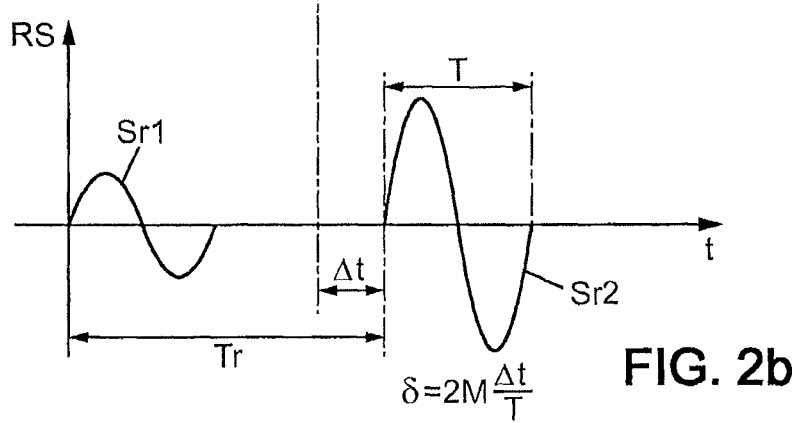
FIG. 2*b* is a time domain curve showing a received sequence of signals corresponding to the emitted sequence of FIG. 2*a*.

FIG. 2b shows the received sequence RS corresponding to the emitted sequence of FIG. 2a, and comprising two received signals Sr1 and Sr2 corresponding to two ultrasound pulses in the received sequence RS. The first received signal Sr1 corresponds to an echo (reflexion) of the first emitted signal Se1, and the second received signal Sr2 corresponding to an echo (reflexion) of the second emitted signal Se2.

In the first configuration of the method, the processing unit 14 further operates the following steps:
c) Calculating a phase difference $\delta$ between the at least two received pulses (sensed by the received signals Sr1, Sr2), relative to the two emitted pulses (emitted signals Se1, Se2, known by the system), and
d) Determining the physical characteristic of the medium at the location P0 on the bases of said phase difference $\delta$.

Each emitted sequence ES of ultrasound waves We comprises several emitted pulses (at least two). Also, each received sequence RS of ultrasound waves Wr comprises several received pulses.

Each pulse in these sequences may be a more complex signal, for example being a combination of a plurality of sine signals. However, we will consider in the present description that the pulses are only sine signals for the sake of simplicity.

A sine signal or pulse comprises a phase $\Phi$ and amplitude X. The phase of such sine signal is the angle at its origin in a time scale representation of the signal. The amplitude is the maximum value of the sine signal over time. Such phase can be determined or estimated by various methods: time shift relative to a reference clock signal, inter-correlation with said reference clock signal, calculation of Arctan(Im/Re) in case the signal is represented by complex values (for example, in case of IQ demodulation), or any other known method.

A phase difference between two sine signals or pulses can be also determined by any one of the above-cited methods, and e.g. simply by differences of predetermined phases of each signal.

Then, the phase difference of step c) can be determined by various methods. Only two of them will be presented in the following description.

According to a first method for determining phases, the phase difference $\delta$ between two sequences of two sine signals (as used in step c) of the method) can be defined as the difference of:

a first phase difference concerning the received signals $\delta_r$, i.e. $\delta_r=\Phi(Sr2)-\Phi(Sr1)$, said first phase difference being measured, and a second phase difference concerning the emitted signals $\delta_e$, i.e. $\delta_e=\Phi(Se2)-\Phi(Se1)$, said second phase difference being known by the system.

The defined phase difference $\delta$ is $\delta=\delta_r-\delta_e$.

This phase difference can also be calculated by the time shifts of the signals relative one to another: in this case, the phase difference $\delta$ is given by:

$$\delta=2.\pi.f.(T_r-T_e)=2.\pi.f.(\Delta t)$$

where f is the frequency of the sine signal, $T_e$ is the time shift between the two emitted signals Se1, Se2 as illustrated on FIG. 2a, and $T_r$ is the time shift between the two received signals Sr1, Sr2 as illustrated on FIG. 2b.

If the time difference $(T_r-T_e)$ is greater than $2.\pi$, it should be reduced to the value modulo $2.\pi$.

According to a second method for determining phases, the two received sine signals may be scaled (weighted) so as to have the same amplitude, and then the resulted weighted signals are subtracted one to the other, i.e.:

$$\delta_r=\Phi(a.Sr2-b.Sr1).$$

Eventually, the first weight coefficient a may be unity, and only $\delta$ is determined so as b.Sr1 has the same amplitude as Sr2.

The inventors have found that the above defined phase difference $\delta$ of the received signals (received pulses) relative to the emitted signals (emitted pulses) surprisingly depends on the nature of the medium 11 at the focused point P0. Therefore, the physical characteristic of said medium at the location P0 can be determined.

This effect is due to the difference of amplitude of first and second emitted pulses (Se1, Se2), and to the non-linear behaviour of the medium at point P0. This non-linear behaviour of medium is usually analysed in ultrasound imaging via amplitude harmonics analysis (second harmonic, third harmonic . . . ). This is an amplitude and frequency analysis. In present case, the method uses phase difference analysis. Of course, such phase technique can also be combined with harmonic analysis.

Advantageously, the first and second emitted signals ultrasound pulses (signals Se1, Se2) have a ratio of amplitudes greater or equal to two.

Additionally, a sum of the emitted signals in the emitted sequence (ES) is null. Therefore, a simple method of summing the received signals cancels the first harmonic and this sum can be directly used to estimate the phase and/or harmonic behaviour of the material in the medium 11.

More specifically, the emit sequence ES can comprise only two emit pulses of inverted amplitudes, denoted as a +1, -1 sequence, such as in pulse inversion method as described in U.S. Pat. No. 6,095,980. In that case, the weighting factors a, b in the above second method for calculating the phase difference should also be preferably (+1, +1) so that the sum of the signals is null.

More specifically, the emit sequence ES can comprise three emit pulses of $+\frac{1}{2}$, $-1$, $+\frac{1}{2}$ amplitudes, such as in power modulated method as described in U.S. Pat. No. 6,638,228. In that case, the above second method for calculating the phase difference should for example use the following formula:

$$\delta_r=\Phi(Sr1+Sr2+Sr3),$$

i.e. having the following weighting factors (+1, +1, +1).

Such method may be generalized as follow:

the emit sequence ES comprises pulses having e1, e2, e3 amplitudes, the received signals Sr1, Sr2, Sr3 are combined into a combined signal CS by weighting factors r1, r2, r3 as follow: CS=r1.Sr1+r2.Sr2+r3.Sr3, and the phase difference $\delta$ is then the phase of the combined signal CS: $\delta=\Phi(CS)$.

In the method, the amplitudes and the weighting factors are chosen so that e1.r1+e2.r2+e3.r3=0. Then, the combined signal CS should be a null signal if the medium at the location P0 behaves as a linear material.

The inventors have discovered that looking at the phase of the resulting signal (the phase of the combined signal), that is the phase difference $\delta$, is representative of the nature of the medium 11 at the location P0.

Thus, the phase difference $\delta$ measured at the given punctual location P0 can be used for determining the type or nature of medium at this punctual location P0.

In a first variant, the physical characteristic PC of the material of medium 11 at or near the punctual location P0 is proportional to the value of the previously determined phase difference $\delta$.

In a second variant, the succession of steps a) to c) are repeated several times, for example M iterations, for providing a plurality of phase differences $\delta$, said plurality having then M values of phase difference: $\delta_1, \ldots, \delta_M$.

Then, during the step d), the physical characteristic PC is determined by:

a mean value of the plurality of phase differences, i.e. PC=mean($\delta_1, \ldots, \delta_M$), or a standard deviation value of the plurality of phase differences, i.e. PC=std($\delta_1, \ldots, \delta_M$), or a variance value of the plurality of phase differences, i.e. PC=variance ($\delta_1, \ldots, \delta_M$), these mathematical functions being usually well known defined or being equivalents of these well-known as many variations in these definitions may be applied.

The M iterations can be proceeded with the same first and second amplitudes for the first and second emitted pulses (signals Se1, Se2) in the emitted sequence ES.

The M iterations can be proceeded with predetermined varying values of amplitudes for the first and second emitted signal Se1, Se2 in the emitted sequence ES, so as to test various variations of amplitudes and to test various possibilities of non-linearities in the medium. Therefore, thanks to the above variant, a non-linear behaviour of the medium 11 at location P0 can be more easily distinguished from a linear behaviour.

In a third variant, the emitted sequence ES may comprise more than two signals of various amplitudes: it may comprise a number N of pulses (signals): three, four, five or even more. The received sequence RS then comprises at least the same number N of received pulses (signals), and preferably the same number N of received pulses (signals). Each received signal Sr1 of index i must be correctly associated to the corresponding emitted signal Sei of same index i.

Then, during the step c), a plurality of couples or pairs (index i and index j, i≠j, and i, j<=N) of emitted-received signals can be extracted, each couple of emitted signals Sei, Sej having a different amplitude. For each couple, a phase difference $\delta ij$ is determined as explained above, so as to provide a plurality of phase differences.

Then, during the step d), the physical characteristic PC is determined by (ij being all the predetermined couples)):
- a mean value of the plurality of phase differences, i.e.: PC=mean($\delta_{ij}$), or
- a standard deviation value of the plurality of phase differences, i.e.: PC=std($\delta_{ij}$), or
- a variance value of the plurality of phase differences, i.e.: PC=variance($\delta_{ij}$).

The above mathematical functions are usually well known defined or equivalent of them.

The N signals may all have different amplitudes or some of them can be identical. Then, various variations of amplitudes can be tested or experienced during the process. Therefore, a non-linear behaviour inside the medium 11 at location P0 can be more easily distinguished from a linear behaviour.

Figure 3A:
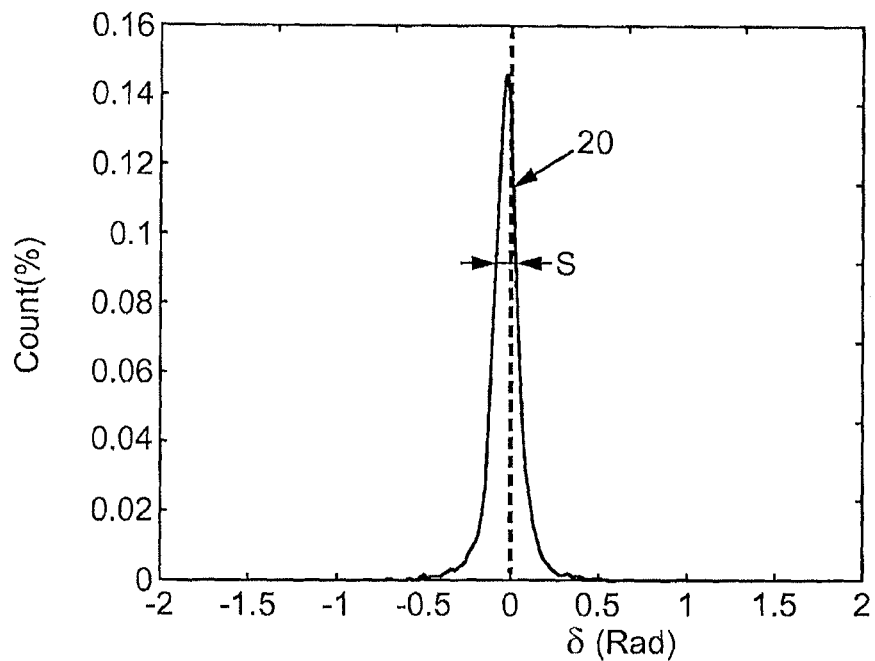
FIG. 3*a* is a distribution of phase difference of received signals relative to emitted signal for a location inside a medium having a quasi-linear material behaviour.

FIG. 3a shows an example of a first distribution 20 of a plurality of phase differences $\delta$ for a location inside a medium having a substantially linear behaviour. Such distribution is a count of a number of tests (ordinate of the curve) providing a given value of phase difference $\delta$ (abscissa of the curve).

This distribution curve 20 comprises a mean value (abscissa of the maximum of the curve) near zero radian, and a small standard deviation or variance (the width S of the curve).

The absolute value of the mean value A is for instance lower than 0.1 radian, and the standard deviation is higher than 0.1 radian.

Such measurement corresponds to a location in the medium 11 having a substantially linear behaviour: It may be a location or region of tissue, or not including any contrast agent (e.g. micro-bubbles).

Figure 3B:
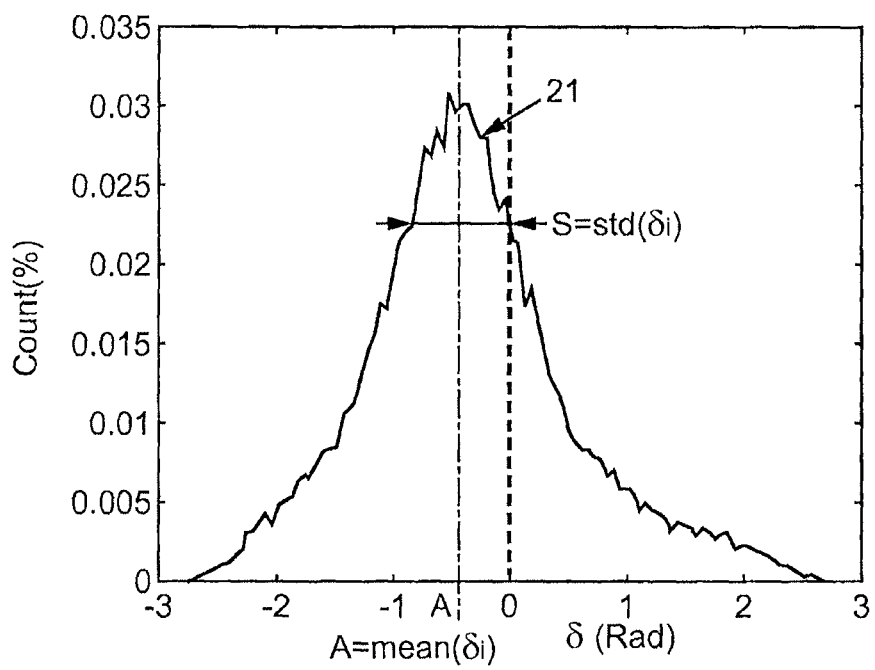
FIG. 3*b* is a distribution of phase difference of received signals relative to emitted signal for a location inside a medium having a non-linear material behaviour.

FIG. 3b shows an example of a second distribution 21 of a plurality of phase differences $\delta$ for a location inside a medium having a substantially non-linear behaviour. It may be a location or region of blood vessel, or including a contrast agent (e.g. micro-bubbles).

This distribution curve 20 comprises a mean value A (abscissa of the maximum of the curve) that is non zero radian, and a standard deviation S or variance much higher (the width of the curve) than in the case of the FIG. 3a.

The absolute value of the mean value A is for instance higher than 0.3 radian, and the standard deviation is higher than 0.3 radian. Both values can therefore be used to distinguish a first type of material (physical characteristic) inside the medium from a second type of material (physical characteristic).

Therefore, all the above variants of the method can then include the following steps for classifying or segmenting the nature or type of physical characteristic at the location P0 inside the medium 11:
- if the physical characteristic PC is lower than or equal to a first limit L1, the physical characteristic corresponds to a first type of material, and
- if the physical characteristic PC is higher than a second limit L2, the physical characteristic corresponds to a second type of material.

Eventually, the second limit L2 is higher than the first limit L1, and if the physical characteristic is inside the interval of these two limits (L1, L2), the type of material is not determined.

Eventually, the second limit L2 is equal to the first limit L1.

Thanks, to these classification steps, the type of physical characteristic is determined.

For example, the first limit L1 is 0.3 radian, or 0.1 radian, so as to determine if the physical characteristic is low (linear behaviour).

For example, the first second limit L2 is 0.3 radian, or 0.5 radian, so as to determine if the physical characteristic is high (non-linear behaviour).

These limits can be adapted to each application of the method: distinguishing a region including a contrast agent from another region not including the contrast agent, or distinguishing tissue to blood vessels, or distinguishing illness cells to healthy cells.

Figure 4:
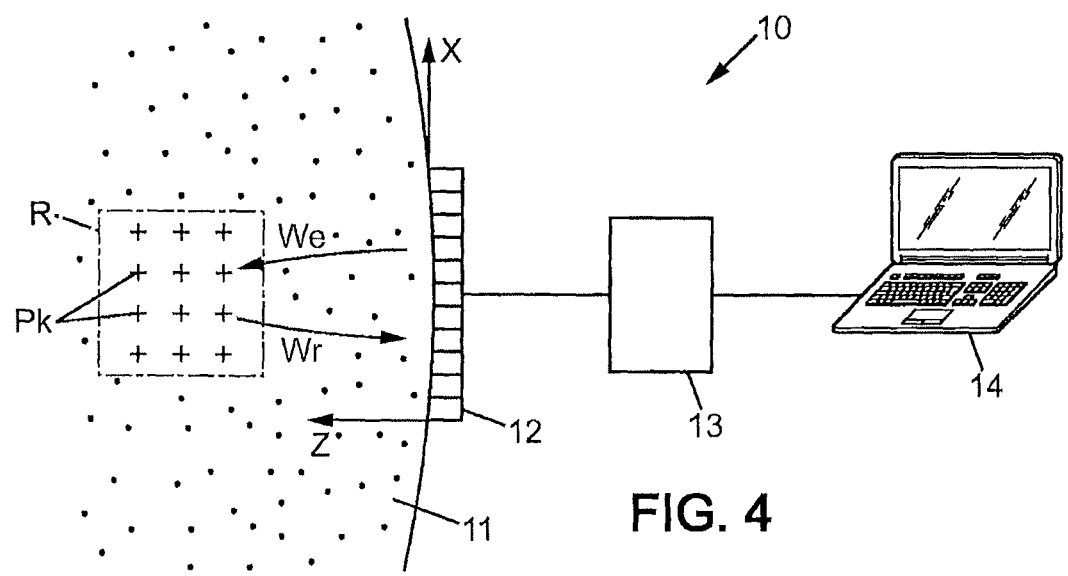
FIG. 4 is a schematic drawing of an apparatus for implementing a second configuration of the method according to the invention (imaging method)

A second configuration of the method is, illustrated on FIG. 4, such method is used for determining an image of a region R inside a medium 11.

The method uses identical or similar elements of the above disclosed apparatus 10 of FIG. 1.

The image produced by the method is composed of a plurality of pixels (for example, a number K of pixels), each pixel corresponding to a different location (Pk) inside the region R, k being an index to identify each pixel in the image or each location in the region R. Eventually, the image may be composed of only one pixel. However, the image may preferably comprise more than one ten thousand pixels (100×100 image).

The second configuration of the method (imaging method) mainly differs from the previous first configuration of the method by the scanning of a plurality of locations inside a region R so as to generate an image of said region.

At each location Pk inside the region R, the processing unit 14 controls the electronic unit 13 and the probe 12 for:
- a) sending an emitted sequence ES of ultrasound waves We towards the location, the emitted sequence ES comprising at least two emitted pulses (corresponding to emitted signals Se1, Se2), said pulses having different amplitudes,
- b) receiving a received sequence RS of ultrasound waves Wr from the location, the received sequence RS comprising at least two received pulses (corresponding to received signals Sr1, Sr2), said received pulses being responses (echoes) from said emitted pulses.

Similarly as for the first configuration, the ultrasound waves We, Wr can be focused or non focused waves, according to known techniques.

The emitted and received signals (representing the pulses) are also similar or identical to those as represented on FIGS. 2a and 2b, and the corresponding above description also applies to the second configuration of the method.

In the method of the second configuration of the invention, the processing unit 14 operates then the following steps for each location Pk inside the region R:
- c) Calculating a phase difference $\delta$ between the two received signals Sr1, Sr2, relative to the two emitted signals Se1, Se2, and
- d) Determining the pixel value in the image, corresponding to the location Pk inside the region R on the bases of the phase difference.

The definitions given for a signal phase and a phase difference $\delta$ during the first configuration of the method are still valid. There are various methods for determining a phase or phase difference.

The phase difference $\delta$ at step c) can be determined by various methods, and least one of the following two methods.

According to a first method, the phase difference $\delta$ is a difference of two phase differences: the one concerning the received signals ($\delta_r$: measured) and the one concerning the emitted signals ($\delta_e$: known). The phase difference is then for example calculated by the following formula (explained in the first configuration of the method):

$$\delta = \delta_r - \delta_e = \Phi(Sr2) - \Phi(Sr1) - \delta_e.$$

Then, the method comprises the following sub-steps:
c1) determining a phase for each one of the two pulses in the received sequence (RS), and
c2) calculating the phase difference δ by subtracting said phases.

According to a second method, the phase difference δ is a phase of a combined signal, said combined signal being a weighted sum of the received signals.

For example, in case of two pulses (signals), the phase difference can be calculated by the following formula:

$$\delta_r = \Phi(a.Sr2 - b.Sr1),$$

The weighting factors a, b being determined to have cancelation of the weighted signals (a.Sr2, b.Sr1) if the medium has a linear behaviour.

More generally, the phase difference δ is:

$$\delta = \Phi(CS) = \Phi(r1.Sr1 + r2.Sr2 + r3.Sr3).$$

The amplitudes e1, e2, e3 for the emit pulses and the weighting factors r1, r2, r3 for the received signals are chosen so that e1.r1+e2.r2+e3.r3=0.

Then, the method comprises the following sub-steps:
c3) received signals corresponding to received pulses are weighted by weighting factors and summed for producing a combined signal CS, the amplitudes of the emit pulses and the weighting factors for the received signals being predetermined so that their inner product is null, and
c4) the phase difference δ is a phase of said combined signal CS. In other words, if amplitudes are firstly defined, the weighting factors are determined so that to compensate the predetermined amplitudes.

In a first variant, the pixel value corresponding to each location Pk inside the region R is directly the value of the previously determined phase difference δ.

In a second variant, the succession of steps a) to c) are repeated several times, for example M iterations, for providing a plurality of phase differences δ, said plurality having then M values of phase difference: $\delta_1, \ldots, \delta_M$.

Then, during the step d), the pixel value is determined by a mean value or standard deviation value or a variance value of the plurality of phase differences.

The M iterations can be proceeded with the same first and second amplitudes for the first and second emitted pulses (signals Se1, Se2) in the emitted sequence ES.

The M iterations can be proceeded with predetermined varying values of amplitudes for the first and second emitted pulses (signals Se1, Se2) in the emitted sequence ES, so as to test various variations of amplitudes and to test various possibilities of non-linearities of the medium at each location Pk. Therefore, a non-linear behaviour of each location Pk in the region can be more easily distinguished from a linear behaviour.

In a third variant, the emitted sequence ES may comprise more than two pulses of various amplitudes: it may comprise a number N of pulses: three, four, five or more pulses. The received sequence RS then comprises at least the same number N of received pulses, and preferably the same number N of received pulses. Each received signal Sr1 of index i (corresponding to a pulse i) must be correctly associated to the corresponding emitted pulse (i.e. emitted signal Sei) of same index i.

Then, during the step c), a plurality of couples or pairs (index i and index j, i≠j, and i, j<=N) of emitted-received signals can be extracted, each couple of emitted signals Sei, Sej having a different amplitude. For each couple, a phase difference δij is determined as explained above, so as to provide a plurality of phase differences.

Then, during the step d), the pixel value is determined by a mean value e or standard deviation value or a variance value of the plurality of phase differences The N emitted pulses (signals) may all have different amplitudes or some of them can be identical. Then, various variations of amplitudes can be tested during the process. Therefore, a non-linear behaviour of the medium 11 at each location Pk inside the region R can be more easily distinguished from a linear behaviour.

In a fourth variant, the region R is subdivided in a plurality of sub-regions, corresponding to sub-area in the image.

Between step c) and step d) of the method, a sub-region phase difference (δsr) is calculated, said sub-region phase difference (δsr) being a mean value of the plurality of phase differences (δ) of the locations belonging to said sub-region calculated during step c).

Then, a pixel in the image corresponds to a sub-region.

Additionally, any of the above variant can be combined to another one to have a method that provides a more sensitive image of the medium: non-linear behaviour are more easily distinguished from a linear behaviour.

Figure 5:
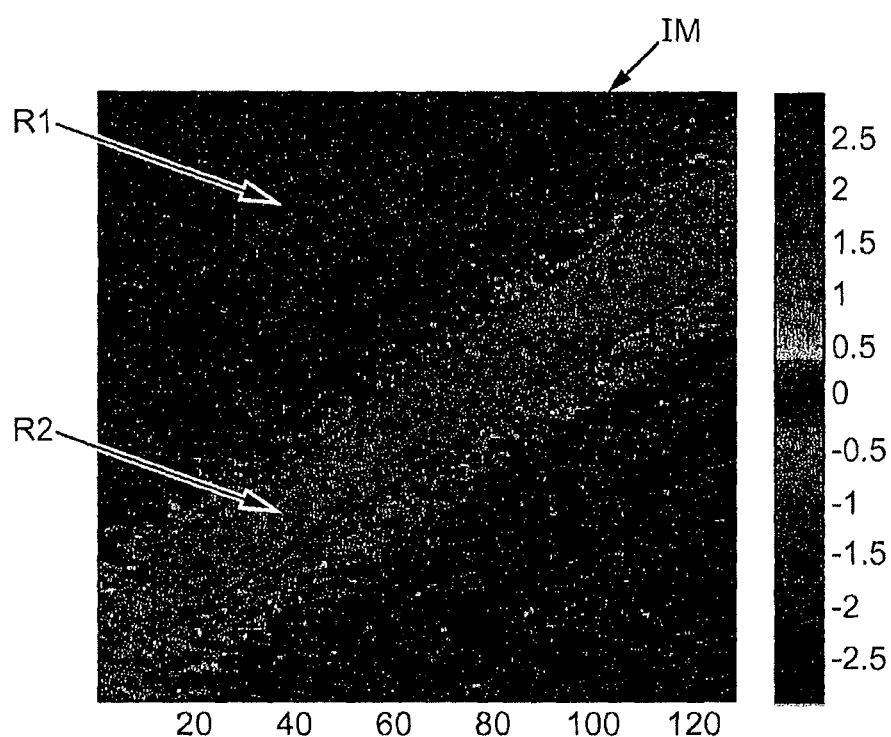
FIG. 5 is an example of image produced by the apparatus and method represented on FIG. 4 and showing two sub-area of segmentation of said image for pointing out two organs included inside the medium.

FIG. 5 shows an example of such image IM determined for a rectangular region inside a body of a patient. The grey scale represents directly the phase difference values determined at each locations of the matrix or grid.

Similarly to the first configuration of the invention, all the variants of the method can then include following steps for classifying or segmenting the image:
if a pixel value is lower than or equal to a first limit L1, the pixel corresponds to a first type and
if a pixel value is higher than a second limit L2, the physical characteristic corresponds to a second type.

Eventually, the second limit L2 is higher than the first limit L1, and if the pixel value is inside the interval of these two limits (L1, L2), the type the pixel is not determined.

Eventually, the second limit L2 is equal to the first limit L1.

Thanks, to these classification steps, the image can be segmented into sub-areas having different properties.

For example, the first limit L1 is 0.3 radian, or 0.1 radian, so as to determine a sub-area of a first type (linear behaviour).

For example, the second limit L2 is 0.3 radian, or 0.5 radian, so as to determine a sub-area of a second type (non-linear behaviour).

These limits can be adapted to each application of the method: distinguishing tissue to blood vessels, or distinguishing illness cells to healthy cells.

For example, the FIG. 5 shows:
a first sub-area R1 of a first type (linear), and being a sub-area corresponding to a portion of the medium 11 being tissue, and
a second sub-area R2 of a second type (non-linear), and being a sub-area corresponding to a portion of the medium 11 being a blood vessel.

Then, in all the present methods can take advantage in using contrast agents inside the medium 11.

For example, contrast agents penetrate blood vessels but not into the tissues. Then, the contrast between the different area of the medium 11 with and without contrast agents will be increased, as illustrated on FIG. 5.

Ultrasound contrast agents could be small gas-filled micro-bubbles contrast agents. Small gas-filled micro-bubbles could be for example seeded into a blood stream or from encapsulated micro-bubbles. Contrast agents could consist of gas-filled microscopically small bubbles encapsulated by an elastic shell. There are a variety of micro-bubbles contrast agents. Micro-bubbles could be heavy gas/air mixture (PFC, SF8), encapsulated (shell—lipid, albumin, polymer). Micro-bubbles differ in their shell makeup, gas core makeup, and whether or not they are targeted. Micro-bubble size is fairly uniform. They lie within a range of 1 to 10 micro-meters in diameter. That makes them smaller than red blood cells, which allows them to flow easily through the circulation as well as the microcirculation. Micro-bubbles could be administered by intravenous injection to the systemic circulation. They could be removed dissolved in circulation, filtered by liver and cleared 15 minutes.

Micro-bubbles have a high degree of ability to reflect the ultrasound waves. When micro-bubbles are caught in an ultrasonic frequency field, they compress, oscillate, and reflect a characteristic echo, generating a non-linear ultrasound backscatter. The ultrasound pulses are thus reflected in a different way by the gas in the medium containing micro-bubbles and by the soft tissue surroundings.

The invention claimed is:

1. A method for determining an image of a region inside a medium, the image being composed of a plurality of pixels, each pixel having a pixel value corresponding to a physical characteristic representing the nature of the medium, wherein the method comprises for one or more locations inside the region, the following steps:
    sending an emitted sequence of ultrasound waves into the medium towards the location, the emitted sequence comprising at least two emitted pulses having different amplitudes,
    receiving a received sequence of ultrasound waves from the location, the received sequence comprising at least two received pulses corresponding to echoes of said emitted pulses,
    calculating a phase difference between the received pulses relative to the emitted pulses,
    determining the image by a succession of sending an emitted sequence of ultrasound waves, receiving a received sequence of ultrasound waves, and calculating a phase difference are repeated several times at each location for providing a plurality of phase differences for each location, and
    wherein each pixel value of the image is determined on the bases of the plurality of phase differences at each location, each pixel corresponding to a location in the medium, and each pixel value corresponding to a physical characteristic of said location in the medium.

2. The method according to claim 1, wherein the step of calculating a phase difference comprises the following substeps:
    determining a phase for each one of the received pulses in the received sequence, and
    calculating the phase difference by combining said phases.

3. The method according to claim 1, wherein the step of calculating a phase difference comprises the following substeps:
    received signals corresponding to said received pulses weighted by weighting factors and summed for producing a combined signal, said weighting factors being determined so that to compensate the different amplitudes of the emit pulses, and
    the phase difference is a phase of said combined signal.

4. The method according to claim 1, wherein the physical characteristic is a value proportional to the value of phase difference.

5. The method according to claim 1, wherein during the determining step, the physical characteristic is determined by a mean or a standard deviation or a variance of said plurality of phase differences.

6. The method according to claim 1, wherein the emitted sequence comprises a number greater than two emitted pulses, the received sequence comprises at least the same number of received pulses than the number of emitted pulses, and wherein:
    during the calculating step, a plurality of phase differences between couples corresponding to two received and emitted pulses is calculated, each couple of emitted pulses having a different amplitude, and
    during the determining step, the physical characteristic is determined by a mean or a standard deviation or a variance of said plurality of phase differences.

7. The method according to claim 1, wherein:
    the region is subdivided in a plurality of sub regions,
    between the calculating step and the determining step, a sub region phase difference is calculated, said sub region phase difference being a mean value of the plurality of phase differences of the locations belonging to said sub region, and
    each pixel in the image corresponds to one sub region.

8. The method according to claim 1, wherein:
    each pixel is of a first type if it the pixel value is lower than or equal to a first limit, and
    each pixel is of a second type if it the pixel value is higher than a second limit.

9. The method according to claim 8, wherein the second limit is higher than the first limit.

10. The method according to claim 8, wherein the first limit is 0.3 radian.

11. The method according to claim 8, wherein the second limit is 0.3 radian.

12. The method according to claim 1, wherein two emitted pulses of the emitted sequence have an amplitude ratio of greater or equal to two.

13. The method according to claim 1, wherein before step, a contrast agent is introduced into the medium.

14. The method according to claim 13, wherein the contrast agents comprises microbubbles.

15. An apparatus for determining an image of a region inside a medium, the image being composed of a plurality of pixels, each pixel having a pixel value corresponding to a physical characteristic representing the nature of the medium of a location in the medium, said apparatus comprising
    a probe comprising an ultrasound transducer or a transducer array,
    an electronic unit controlling the transducer or transducer array, and
    a processing unit for controlling the electronic unit and for processing signals from said electronic unit, and
wherein the probe and electronic unit are configured to perform:
    sending an emitted sequence of ultrasound waves into the medium towards one or more locations into the region, the emitted sequence comprising at least two emitted pulses having different amplitudes, receiving a received sequence of ultrasound waves from the one or more locations, the received sequence comprising at least two received pulses corresponding to echoes of said emitted pulses, wherein the processing unit comprises a computer for processing signals corresponding to the received sequence and for:

calculating a phase difference between the received pulses relative to the emitted pulses, determining the image by a succession of sending an emitted sequence of ultrasound waves, receiving a received sequence of ultrasound waves, and calculating a phase difference are repeated several times at each location for providing a plurality of phase differences for each location, and wherein each pixel value of the image is determined on the bases of the plurality of phase differences at each location, each pixel corresponding to a location in the medium, and each pixel value corresponding to a physical characteristic of said location in the medium.

* * * * *